(12) United States Patent
Rode et al.

(10) Patent No.: US 6,403,833 B1
(45) Date of Patent: Jun. 11, 2002

US006403833B1

(54) SINGLE STEP HYDROGENATION OF NITROBENZENE TO P-AMINOPHENOL

(75) Inventors: Chandrashekhar Vasant Rode; Manisha Jagdeeshrao Vaidya; Raghunath Vitthal Chaudhari, all of Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/774,255

(22) Filed: Jan. 30, 2001

(51) Int. Cl.[7] ............................................. C07C 209/36
(52) U.S. Cl. ........................ 564/394; 564/418; 564/422; 564/423
(58) Field of Search ................................ 564/394, 418, 564/422, 423

(56) References Cited

U.S. PATENT DOCUMENTS 3,715,397 A * 2/1973 Rylander et al. ............ 564/418

FOREIGN PATENT DOCUMENTS

| DE | 2311038 | 9/1974 |
| EP | 0 041 837 | 12/1981 |
| EP | 0 211 545 | 2/1987 |
| FR | 1559841 | 3/1969 |
| FR | 2618428 | 1/1989 |
| WO | WO 93/20039 | 10/1993 |

OTHER PUBLICATIONS

Gowda et al., 'Nickel–catalyzed formic acid reductions. A selective method for the reduction of nitro compounds.' Synthetic Comm. 30(16), 2000, pp. 2889–2895.*

EPO Search Report from EPO for Application No. 01300872.7–2103 dated May 23, 2001.

* cited by examiner

Primary Examiner—Brian J. Davis
(74) Attorney, Agent, or Firm—Darby & Darby

(57) ABSTRACT

The present invention provides a single step process for the preparation of p-aminophenol by hydrogenation of nitrobenzene in presence of an aqueous acid over a mono or bimetallic nickel catalyst at a temperature in the range of 80–120° C. for a period of 1 to 4 hrs. The resulting reaction mixture is extracted with an organic solvent like ethyl acetate, cyclohexane or toluene to separate the aqueous layer containing PAP and neutralizing it with ammonia solution to recover the solid p-aminophenol.

5 Claims, No Drawings

SINGLE STEP HYDROGENATION OF NITROBENZENE TO P-AMINOPHENOL

FIELD OF THE INVENTION

The present invention relates to a single step hydrogenation process for the preparation of p-aminophenol. More particularly, the process relates to the preparation of p-aminophenol in an aqueous acid medium using mono and bimetallic nickel catalysts.

Background of the Invention p-Aminophenol (PAP) is a well known and very careful industrial chemical. It is used as an intermediate in the production of pharmaceuticals such as paracetamol, in the production of dyestuffs such as sulphur dyes and in making photographic chemicals.

Conventionally, PAP is prepared by hydrolysing p-nitrochlorobenzene to p-nitrophenol. Hydrogenation of p-nitrophenol to PAP is then carried out using Fe/HCl catalyst. In this multi-step process, quantity of iron (catalyst precursor) required is quite large, subsequently the production of iron—iron oxide sludge is large, posing a serious effluent problem. The work-up of reaction crude is cumbersome. The quantity of iron used is very important for the faster reduction rate.

An important commercial process for the preparation of p-aminophenol involves the catalytic hydrogenation of nitrobenzene in acidic medium using supported platinum based catalysts. In this process phenylhydroxylamine (PHA) is first formed and this intermediate immediately rearranges in the presence of acid to PAP. The major by-product formed is aniline. In actual practice, both these steps are carried out in a single reactor. The reaction mixture consists of both aqueous as well as organic phases.

Reference may be made to U.S. Pat. No. 3,383,416; 1969 by Benner wherein the catalyst reported was Pt/C for hydrogenation of nitrobenzene to p-aminophenol. Greco (U.S. Pat. No. 3,953,509; 1976) reported the use of molybdenum sulphide on carbon catalyst for the hydrogenation of nitrobenzene to PAP. Dunn (U.S. Pat. No. 4,264,529; 1981) has reported the use of platinum on γ-alumina for the hydrogenation of nitrobenzene to yield PAP. Low temperature hydrogenation in the presence of modified catalyst system containing sulphur compound and the rearrangement step in a separate vessel has been suggested by Caskey and Chapman (U.S. Pat. No. 4,415,753; 1983). Rylander et al. (U.S. Pat. No. 3,715,397; 1973) disclosed a process for preparation of PAP by catalytic hydrogenation of nitrobenzene in a sulphuric acid medium in the presence of dimethylsulfoxide, using platinum oxide catalyst.

Thus, the catalysts used for hydrogenation of nitrobenzene to p-aminophenol reported in the literature are Pt, Pd, Ru, and $PtO_2$. Among these catalysts, however, Pt is the most active for this system but it is very costly. All these being noble metal the process becomes cost intensive. It also demands to use the same catalyst for several times and also to recover the metal from deactivated catalyst in order to make the process economical.

p-Aminophenol is an important raw material for making paracetamol which is widely used in antipyretic and analgesic drug formulations. Conventional method for preparation of p-aminophenol (PAP) involves reduction of nitrophenol with Fe—HCl. This process suffers from major drawbacks such as formation of large amount of sludge (1.2 kg sludge/kg product) posing serious effluent problems and cumbersome work up of reaction crude to obtain pure PAP. Alternate process for PAP involves the catalytic hydrogenation of nitrobenzene using supported platinum catalyst in presence of aqueous acid.

In accordance with this invention, it has now been discovered that group VIII metal like nickel alone or combination of nickel with traces of noble metals like Pt or Pd can be used as an efficient and cheaper catalyst system for hydrogenation of nitrobenzene to PAP. Complete conversion of nitrobenzene is achieved to give PAP as the major product with aniline as a side product.

Objects of the Invention

The main object of the present invention is to provide mono and bimetallic catalysts for single step hydrogenation of nitrobenzene to p-aminophenol, which obviates the drawbacks as detailed above.

SUMMARY OF THE INVENTION

The present invention provides a single step process for the preparation of p-aminophenol by hydrogenation of nitrobenzene in presence of an aqueous acid over a mono or bimetallic Ni catalyst, terminating the reaction to obtain a reaction mixture containing the product, extracting the reaction mixture with an organic solvent, separating the aqueous layer containing PAP and neutralising with ammonia solution to separate the solid product.

The present invention provides a single step process for the preparation of p-aminophenol which comprises contacting a mixture of nitrobenzene and aqueous acid with hydrogen over a Ni containing catalyst at a hydrogen pressure upto 1000 psig, at a temperature in the range of 80–120° C. for a period of 1 to 4 hrs, terminating the reaction to obtain a reaction mixture containing the product, extracting the reaction mixture with an organic solvent, separating the aqueous layer containing the product, adjusting it's pH to 7–8 to get solid p-aminophenol.

Accordingly the present invention provides a process for the single step hydrogenation of nitrobenzene to p-aminophneol, said process comprising (a) contacting a mixture of nitrobenzene and aqueous acid with hydrogen mono or bimetallic catalyst at a pressure upto 700 psi, at a temperature 80–120° C. for a period of 1–4 hrs, (b) terminating the reaction to obtain product mixture, (c) removing the reaction mixture from the autoclave, (d) separating the catalyst and resin from the reaction mixture by filtration, (e) extracting the filtrate with toluene, (f) analysing the organic and aqueous layers for reactants and products using GC and PLC, (g) treating the aqueous layer with ammonia solution to adjust the pH of solution to 3–4 to partly precipitate PAP, (h) separating the solid thus obtained by filtration, (i) extracting the filtrate with toluene, (j) treating the aqueous layer with ammonia solution to pH 7–8 to substantially precipitate PAP, (k) washing the total solid thus obtained after first and second extraction with distilled water, drying and weighing.

In one embodiment of the invention, the catalyst comprises 10% Ni on a solid support selected from the group consisting of silica, ZSM-5, clay and carbon.

In another embodiment of the invention, a bimetallic catalyst comprising of Ni and traces of one of the group VII metals is used as a catalyst system to increase the selectivity of p-aminophenol.

In yet another embodiment of the present invention, the temperature of the reaction ranges between 80–120° C.

In still another embodiment of the present invention, the concentration of acid used is ranges between 2.5–10% w/w.

In another embodiment of the present invention, Pt content of the catalyst is in the range of 0.05–3%.

In another embodiment of the present invention, Ni content of the catalyst is in the range of 5–20%.

In another embodiment the organic solvent used for the extraction of reaction mixture may be selected from toluene, cyclohexane, ethyl acetate of alike.

DETAILED DESCRIPTION OF THE INVENTION

The following examples are given by way of illustration and therefore should not be construed to limit the scope of present invention.

EXAMPLE 1
Preparation of powdered 10% Ni/ZSM-5 catalyst.

Monometallic Ni supported on zeolite catalyst was prepared by precipitation technique following the procedure as given: The support (5 gm) zeolite ZSM-5 (Si/Al=20) was calcined for 4 hours before use at 773 K. A slurry of the support was made in distilled water, stirred for 2 hrs at 363 K. To this hot solution, 2.47 gm of Ni $(NO_3)_2.6H_2O$ was added. After stirring for 6 hrs, 10% ammonium carbonate solution was added dropwise. The addition continued till a pH value of 10 was attained. The resulting slurry was filtered to obtain a green cake and a colourless filtrate confirming the complete precipitation of Ni as nickel carbonate. The AAS analysis revealed the absence of Ni in the filtrate. The cake was dried overnight at 383 K and was calcined in a static air furnace at 773 K for 10 hrs. The reduction was carried out in an activation furnace using Silica-quartz tube at 773 K at hydrogen flow rate of $5 \times 10^{-5}$ $m^3$/min. for 10 hrs.

EXAMPLE 2

For bimetallic catalyst, the monometallic 10% Ni/ZSM-5 catalyst before calcination is charged to a toluene solution containing Pt $(C_8H_{12})Cl_2$ as Pt precursor. This suspension was refluxed for 4 hrs and the excess toluene was removed using a rotavapor. The powder obtained was calcined in static air at 773 K for 10 hrs. The reduction of the catalyst was carried out in an activation furnace using Silica-quartz tube at 773 K at hydrogen flow rate of $5 \times 10^{-5}$ $m^3$/min. for 10 hrs.

EXAMPLE 3

PAP was prepared by single step catalytic hydrogenation of nitrobenzene in a stirred 0.3 liter hastelloy autoclave having an automatic temperature controller. A reaction charge was prepared by adding 10 gm (0.0813 mol) of nitrobenzene, 85 gm water, 0.20 gm 10% Ni/C catalyst and 5.5 gm (3 ml) sulphuric acid. The reactor was sealed, purged initially with nitrogen and then with hydrogen. When the reaction temperature was attained to 120° C., the reactor was pressurised to 400 psig with $H_2$ and the reaction was commenced by starting the agitation. The temperature was controlled during the reaction in the range of 118–122° C. Hydrogen uptake was monitored with pressure gauge as a function of time. When hydrogen uptake stopped abruptly indicating the end of reaction (after slightly more than 2 moles of hydrogen per mole of nitrobenzene was consumed), the reaction was stopped. After completion of reaction, the reactor was purged with nitrogen, the reaction mixture was removed from the autoclave and the catalyst was separated from the reaction mixture by filtration. The filtrate was extracted with toluene. The organic and aqueous layers were analysed for reactants and products using GC and HPLC. The aqueous layer was treated with ammonia solution to adjust the pH of solution to 3–4, when PAP is precipitated partly. The solid thus obtained is separated by filtration. Again the filtrate is extracted with toluene and aqueous layer is treated with ammonia solution to pH 7–8 when maximum amount of PAP is precipitated. The total solid thus obtained after first and second extraction is washed with distilled water, dried and weighed. The conversion of nitrobenzene was found to be 14% and selectivity of PAP was found to be 14% and 86% to aniline.

EXAMPLE 4

In a typical experiment, 10 gm of nitrobenzene, 85 gm of water, 0.2 gm of 10% Ni/$SiO_2$ catalyst and 3 ml sulphuric acid were added to the reactor. The reaction was carried out at 120° C. and hydrogen pressure of 400 psig. After completion of reaction the reactor was cooled, catalyst was separated by filtration and washed and extracted with toluene. The solid PAP was recovered from aqueous layer by neutralisation with ammonia solution. Aqueous and organic layers were analysed by GC and HPLC. The conversion of nitrobenzene was found to be 30% with 11% selectivity to PAP and 89% selectivity to aniline.

EXAMPLE 5

In a typical experiment, 10 gm of nitrobenzene, 85 gm of water, 0.2 gm of 10% Ni/ZSM-5 catalyst and 3 ml sulphuric acid were added to the reactor. The reaction was carried out at 120° C. and hydrogen pressure of 400 psig. After completion of reaction the reactor was cooled, catalyst was separated by filtration, washed and extracted with toluene. The solid PAP was recovered from aqueous layer by neutralisation with ammonia solution. Aqueous and organic layers were analysed by GC and HPLC. The conversion of nitrobenzene was found to be 45% with 45% selectivity to PAP and 55% selectivity to aniline.

EXAMPLE 6

In a typical experiment, 10 gm of nitrobenzene, 85 gm of water, 0.2 gm of 10% Ni-0.05% Pt/ZSM-5 catalyst and 3 ml sulphuric acid were added to the reactor. The reaction was carried out at 120° C. and hydrogen pressure of 400 psig. After completion of reaction the reactor was cooled, catalyst was separated by filtration and washed and extracted with toluene. The solid PAP was recovered from aqueous layer by neutralisation with ammonia solution. Aqueous and organic layers were analysed by GC and HPLC. The conversion of nitrobenzene was found to be 49% with 11% selectivity to PAP and rest to aniline.

EXAMPLE 7

In a typical experiment, 10 gm of nitrobenzene, 85 gm of water, 0.2 gm of 10% Ni-0.1% Pt/ZSM-5 catalyst and 3 ml sulphuric acid were added to the reactor. The reaction was carried out at 120° C. and hydrogen pressure of 400 psig. After completion of reaction the reactor was cooled, catalyst was separated by filtration and washed and extracted with toluene. The solid PAP was recovered from aqueous layer by neutralisation with ammonia solution. Aqueous and organic layers were analysed by GC and HPLC. The conversion of nitrobenzene was found to be 42% with 25% selectivity to PAP and 75% selectivity to aniline.

EXAMPLE 8

In a typical experiment, 10 gm of nitrobenzene, 85 gm of water, 0.2 gm of 10% Ni-1% Pt/ZSM-5 catalyst and 3 ml sulphuric acid were added to the reactor. The reaction was carried out at 120° C. and hydrogen pressure of 400 psig. After completion of reaction the reactor was cooled, catalyst was separated by filtration and washed and extracted with toluene. The solid PAP was recovered from aqueous layer by neutralisation with ammonia solution. Aqueous and organic layers were analysed by GC and HPLC. The conversion of nitrobenzene was found to be 93% with 63% selectivity to PAP and 45% selectivity to aniline.

EXAMPLE 9

In a typical experiment, 10 gm of nitrobenzene, 85 gm of water, 0.2 gm of 10% Ni-1% Pt/ZSM-5 catalyst and 3 ml sulphuric acid were added to the reactor. The reaction was carried out at 80° C. and hydrogen pressure of 400 psig. After completion of reaction the reactor was cooled, catalyst was separated by filtration and washed and extracted with toluene. The solid PAP was recovered from aqueous layer by neutralisation with ammonia solution. Aqueous and organic layers were analysed by GC and HPLC. The conversion of nitrobenzene was found to be 100% with 25% selectivity to PAP and 75% selectivity to aniline.

EXAMPLE 10

In a typical experiment, 10 gm of nitrobenzene, 85 gm of water, 0.1 gm of 10% Ni-1% Pt/ZSM-5 catalyst and 3 ml sulphuric acid were added to the reactor. The reaction was carried out at 120° C. and hydrogen pressure of 400 psig. After completion of reaction the reactor was cooled, catalyst was separated by filtration and washed and extracted with toluene. The solid PAP was recovered from aqueous layer by neutralisation with ammonia solution. Aqueous and organic layers were analysed by GC and HPLC. The conversion of nitrobenzene was found to be 99% with 45% selectivity to PAP and 55% selectivity to aniline.

EXAMPLE 11

In a typical experiment, 10 gm of nitrobenzene, 85 gm of water, 0.1 gm of 10% Ni-3% Pt/ZSM-5 catalyst and 3 ml sulphuric acid were added to the reactor. The reaction was carried out at 120° C. and hydrogen pressure of 400 psig. After completion of reaction the reactor was cooled, catalyst was separated by filtration and washed and extracted with toluene. The solid PAP was recovered from aqueous layer by neutralisation with ammonia solution. Aqueous and organic layers were analysed by GC and HPLC. The conversion of nitrobenzene was found to be 35% with 65% selectivity to PAP and 79% selectivity to aniline.

EXAMPLE 12

In a typical experiment, 10 gm of nitrobenzene, 85 gm of water, 0.1 gm of 10% Ni-1% Pd/ZSM-5 catalyst and 3 ml sulphuric acid were added to the reactor. The reaction was carried out at 120° C. and hydrogen pressure of 400 psig. After completion of reaction the reactor was cooled, catalyst was separated by filtration and washed and extracted with toluene. The solid PAP was recovered from aqueous layer by neutralisation with ammonia solution. Aqueous and organic layers were analysed by GC and HPLC. The conversion of nitrobenzene was found to be 99% with 20% selectivity to PAP and 79% selectivity to aniline.

We claim:

1. A process for the single step hydrogenation of nitrobenzene to p-aminophenol, said process comprising:

(a) contacting a mixture of nitrobenzene and aqueous acid with a Ni-containing hydrogen mono or bimetallic catalyst at a pressure up to 700 psi, at a temperature of from 80–120° C. for a period of from 1–4 hrs, (b) terminating the reaction to obtain product mixture, (c) removing the reaction mixture from the autoclave, (d) separating the catalyst and resin from the reaction mixture by filtration, (e) extracting the filtrate with toluene, (f) analyzing the organic and aqueous layers for reactants and products using GC and PLC, (g) treating the aqueous layer with ammonia solution to adjust the pH of solution to 3–4 to partly precipitate PAP, (h) separating the solid thus obtained by filtration, (i) extracting the filtrate with toluene, (j) treating the aqueous layer with ammonia solution to pH 7–8 to substantially precipitate PAP, and (k) washing the total solid thus obtained after first and second extraction with distilled water, drying and weighing.

2. A process as claimed in claim 1, wherein the bimetallic catalyst employed is selected from the group consisting of Ni—Pt and Ni—Pd.

3. A process as claimed in claim 1 wherein the Ni content in the monometallic catalyst is from 5–20 weight %.

4. A process as claimed in claim 1, wherein the Ni-containing mono or bimetallic catalyst is a bimetallic catalyst which further comprises Pt.

5. A process as claimed in claim 4 wherein the Pt content of the bimetallic catalyst is from 0.05–3 weight %.

* * * * *